(12) United States Patent
Bradley et al.

(10) Patent No.: US 8,059,628 B2
(45) Date of Patent: Nov. 15, 2011

(54) LOW POWER MULTIPLE CHANNEL MIXING ARCHITECTURE FOR DETECTING WAKE-UP SIGNALS AND RELATED FALSING PROTECTION ALGORITHM

(75) Inventors: Peter Bradley, San Diego, CA (US); Guy A. Delight, Escondido, CA (US); Remi Le Reverend, San Diego, CA (US); Philip Dorning, Wiltshire (GB); Andrew M. Bottomley, San Diego, CA (US); Eric D. Corndorf, Minneapolis, MN (US); Charles H. Dudding, Lino Lakes, MN (US); Nicholas C. Wine, Minneapolis, MN (US); George C. Rosar, Minneapolis, MN (US); Quentin Scott Denzene, Andover, MN (US); Robert S. Wentink, Lino Lakes, MN (US)

(73) Assignee: Medtronic, Inc., Minneapolis, MN (US)

( * ) Notice: Subject to any disclaimer, the term of this patent is extended or adjusted under 35 U.S.C. 154(b) by 134 days.

(21) Appl. No.: 12/364,432

(22) Filed: Feb. 2, 2009

(65) Prior Publication Data

US 2009/0252042 A1 Oct. 8, 2009

Related U.S. Application Data

(60) Provisional application No. 61/043,093, filed on Apr. 7, 2008.

(51) Int. Cl.
*H04J 1/00* (2006.01)
*H04W 4/00* (2009.01)
*A61N 1/00* (2006.01)
*G06F 11/00* (2006.01)

(52) U.S. Cl. .......... 370/343; 370/241; 370/340; 607/32; 607/60; 128/903; 600/300

(58) Field of Classification Search .................. None
See application file for complete search history.

(56) References Cited

U.S. PATENT DOCUMENTS

| 4,676,248 A | 6/1987 | Berntson |
| 4,747,101 A | 5/1988 | Akaiwa |
| 5,625,889 A | 4/1997 | Chikkaswamy |

(Continued)

OTHER PUBLICATIONS

Zarlink Semiconductor, ZL70100: Medical Implantable RF Transceiver, Data Sheet, May 2005, 6 Pages.

(Continued)

*Primary Examiner* — Ricky Ngo
*Assistant Examiner* — Clemence Han
(74) *Attorney, Agent, or Firm* — Stephen W. Bauer; Michael J. Ostrom

(57) ABSTRACT

A low power multiple channel receiver mixing architecture for detecting wake-up signals over multiple communication channels in sniff processing performed in an implantable medical device (IMD). The architecture includes a direct conversion real receiver configured to scan a selected center channel and a Weaver receiver configured in parallel to the direct conversion real receiver to simultaneously scan side channels, together simultaneously detecting whether a wake-up signal is being received over the center and side channels with minimal power consumption. The architecture further utilizes a falsing protection algorithm that reduces power consumption during sniff operations by inhibiting the sniffing of channels likely to provide a false indication of a wake-up signal based the presence of unwanted signals on those channels. The falsing protection algorithm restricts those channels from sniff processing likely to provide a false indication of a wake-up signal, such that sniff processing can aborted, prevented, limited or otherwise altered to conserve power consumption.

28 Claims, 10 Drawing Sheets

U.S. PATENT DOCUMENTS

| | | | |
|---|---|---|---|
| 5,715,235 A * | 2/1998 | Sawahashi et al. | 370/206 |
| 6,081,697 A | 6/2000 | Haartsen | |
| 2003/0035388 A1 * | 2/2003 | Schmidt | 370/329 |
| 2003/0114897 A1 | 6/2003 | Von Arx | |
| 2003/0114898 A1 | 6/2003 | Von Arx | |
| 2005/0220135 A1 | 10/2005 | Honda | |
| 2006/0058001 A1 | 3/2006 | Minnis et al. | |
| 2006/0202798 A1 | 9/2006 | Baumgartner | |
| 2007/0049983 A1 * | 3/2007 | Freeberg | 607/32 |
| 2008/0215121 A1 * | 9/2008 | Bange et al. | 607/60 |
| 2009/0168849 A1 * | 7/2009 | Rouxel | 375/140 |

OTHER PUBLICATIONS

Panescu, "Emerging Technologies, Wireless Communication Systems for Implantable Medical Devices," IEEE Engineering in Medicine and Biology Magazine, Mar./Apr. 2008, pp. 96-101.

International Search Report/PCTUS2009/037250, 4 pages.

* cited by examiner

LOW POWER MULTIPLE CHANNEL MIXING ARCHITECTURE FOR DETECTING WAKE-UP SIGNALS AND RELATED FALSING PROTECTION ALGORITHM

RELATED APPLICATION

This application claims the benefit of and priority to U.S. Provisional Application Ser. No. 61/043,093, filed Apr. 7, 2008, entitled, "Low Power Multiple Channel Mixing Architecture For Detecting Wake-Up Signals and Related Falsing Protection Algorithm," the contents of which are incorporated by reference herein in its entirety.

TECHNICAL FIELD

This disclosure relates generally to implantable medical devices (IMDs) and more particularly to IMDs capable of telemetry.

BACKGROUND

A wide variety of IMDs have been developed in order to monitor patient conditions and deliver therapy to the patient. An IMD typically includes a hermetically sealed housing coupled to one or more leads that are surgically implanted inside a patient for sensing conditions or for administering therapy. The IMD may provide therapeutic stimulation to the patient or may deliver drugs or agents to the patient. Alternatively or additionally, the IMD may have sensing or monitoring capabilities. For example, the IMD may sense information within a patient and store the sensed information for subsequent analysis. In some cases, the sensed information may be used directly by the IMD to adjust or control the therapy that is delivered to the patent. Telemetry is used to communicate sensed information from the IMD to an external medical device so that analysis of the sensed information can be performed. Telemetry is further used to communicate information or instructions from external medical devices to the IMD. The IMD includes a telemetry module for performing such telemetry.

Special frequency bands have been allocated for implantable medical devices using RF telemetry, such as the MICS (Medical Implantable Communication Service) band ranging from 402-405 MHz and the MEDS (Medical Electronic Data Service) band that extends the range to 401-406 MHz. The limited battery capacity in IMDs presents a challenge in operating a RF transceiver at such frequencies. One manner employed to conserve power in an IMD is to maintain the IMD in an off state and operate in the so-called "sniff" mode. This means that the complete receiver RF portion of the device is turned on for a limited period of time (e.g. 10 milliseconds) during which time the device listens to see if there are any transmitters active in the vicinity wanting to make contact with the IMD. By duty cycling the on (sniff) time heavily with the off time a considerable power saving can be achieved. The signals received during these sniff operations are referred to as wake-up signals that direct the IMD to power on various components to communicate with the external medical device.

SUMMARY

In one or more embodiments, an implantable medical device (IMD) and method are provided in which a telemetry module in the IMD is normally maintained in a low power inactive "sleep" state and powered up to perform sniff operations on communication channels for detecting the presence of wake-up signals. In one or more embodiments, the IMD includes a multiple channel mixing architecture including a direct conversion real receiver circuit and a Weaver image rejecting mixer receiver circuit. The direct conversion real receiver circuit is configured when activated to monitor or scan a selected communication channel to detect whether a wake-up signal is being received from a remote device over the selected communication channel. The selected communication channel is designated as the center channel. The Weaver image rejecting mixer receiver circuit is configured in parallel to the direct conversion real receiver to simultaneously scan at least one communication channel adjacent to the selected communication channel (designated as so called "side channels") to detect whether a wake-up communication signal is being received over the side channels.

In one or more embodiments, the direct conversion real receiver and the Weaver image rejecting mixer receiver are configured to simultaneously scan the center and side channels whilst maintaining good signal selectivity so as to be able to individually detect whether a wake-up signal is being received over a specific one of the scanned communication channels. In one or more embodiments, sniff operations are able to be performed simultaneously on multiple communication channels efficiently using a receiver having a low power multiple channel mixing architecture.

In one or more embodiments, an IMD employing a falsing protection algorithm is provided that reduces power consumption in the IMD during sniff operations by inhibiting the sniffing of communication channels that are likely to provide a false indication of a wake-up signal based upon noise, interference or other unwanted signals that are present within those channels. The falsing protection algorithm restricts those channels from sniff processing that are likely to provide such a false indication of a wake-up signal, where sniff processing can be aborted, prevented, limited or otherwise altered if a channel becomes restricted.

DRAWINGS

The above-mentioned features and objects of the present disclosure will become more apparent with reference to the following description taken in conjunction with the accompanying drawings wherein like reference numerals denote like elements and in which.

DETAILED DESCRIPTION

Since the battery capacity in an IMD is very limited, the power consumed by the components of the IMD can be conserved by keeping the components in a power off or low power "sleep" state when they are not being utilized. The present disclosure describes an implantable medical device (IMD) and a method for operating the same in which multiple communication channels accessible by the IMD can be simultaneously sniffed for wake-up signals using a Weaver receiver architecture in combination with a direct conversion receiver in order to minimize total power consumption. The present disclosure further describes a falsing protection algorithm that reduces power consumption in the IMD during such sniff operations by inhibiting the sniffing of channels that are likely to provide a false indication of a wake-up signal. In the following description, numerous embodiments are set forth in order to provide a thorough understanding of the invention. It will be apparent, however, to one skilled in the art, that these and other embodiments may be practiced without these specific details. In some instances, features well-known to those skilled in the art have not been described in detail in order not to obscure the present disclosure.

Figure 1:
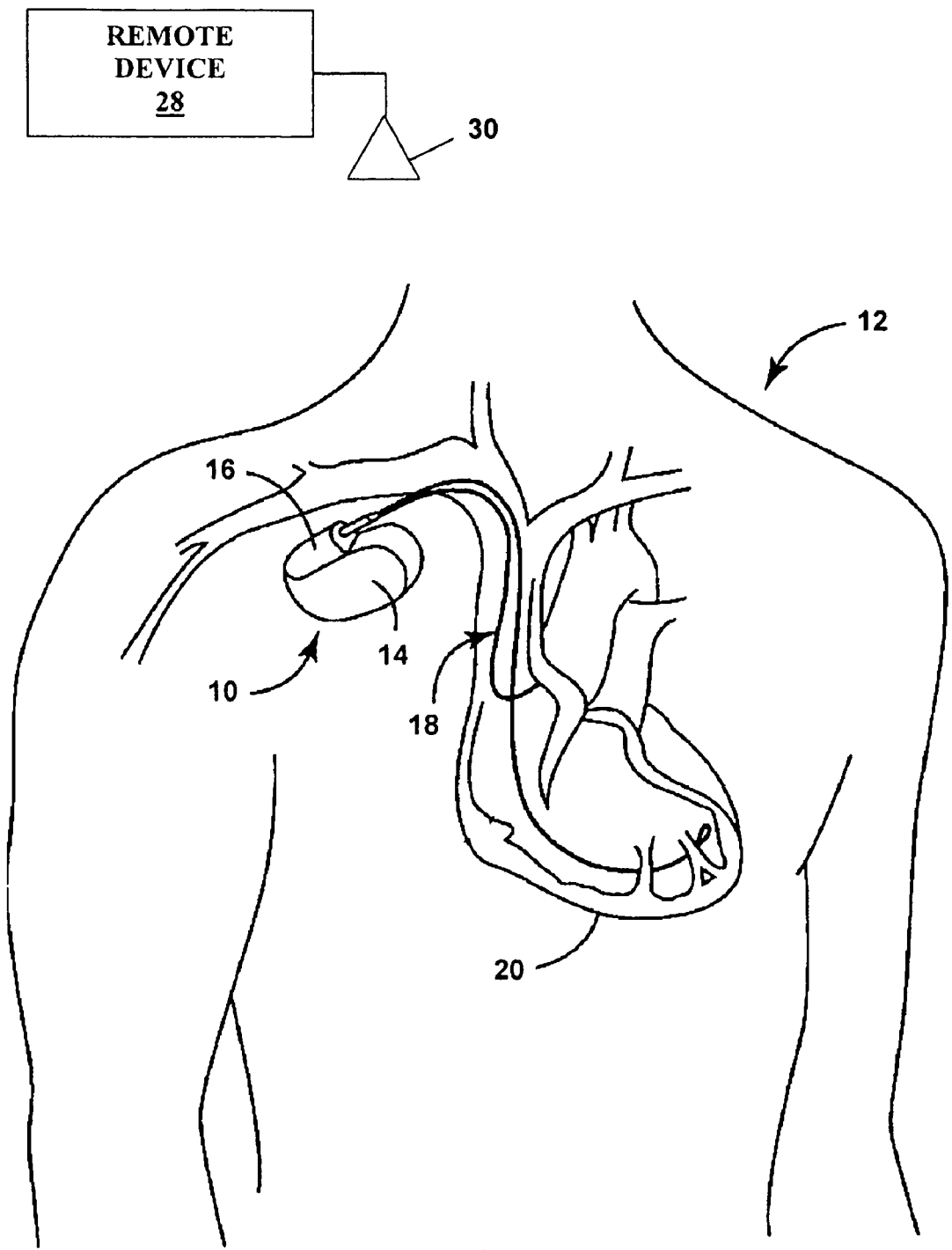
FIG. 1 illustrates an implantable medical device system in accordance with an embodiment of the present disclosure implanted in a human body.

FIG. 1 is a simplified schematic view of one embodiment of implantable medical device ("IMD") 10 of the present disclosure implanted within a human body 12. IMD 10 comprises a hermetically sealed enclosure 14 and connector module 16 for coupling IMD 10 to electrical leads 18 arranged within body 12, such as pacing and sensing leads 18 connected to portions of a heart 20 for delivery of pacing pulses to a patient's heart 20 and sensing of heart 20 conditions. While IMD 10 is depicted in a pacemaker device configuration in FIG. 1, it is understood that IMD 10 may comprise any type of implanted device including, but not limited to implantable cardioverter-defibrillators (ICDs), an implantable combination pacemaker-cardioverter-defibrillator (PCDs), implantable brain stimulators, implantable gastric system stimulators, implantable nerve stimulators or muscle stimulators, implantable lower colon stimulators, implantable drug or beneficial agent dispensers or pumps, implantable cardiac signal loops or other types of recorders or monitors, implantable gene therapy delivery devices, implantable incontinence prevention or monitoring devices, implantable insulin pumps or monitoring devices, and so on.

Figure 2:
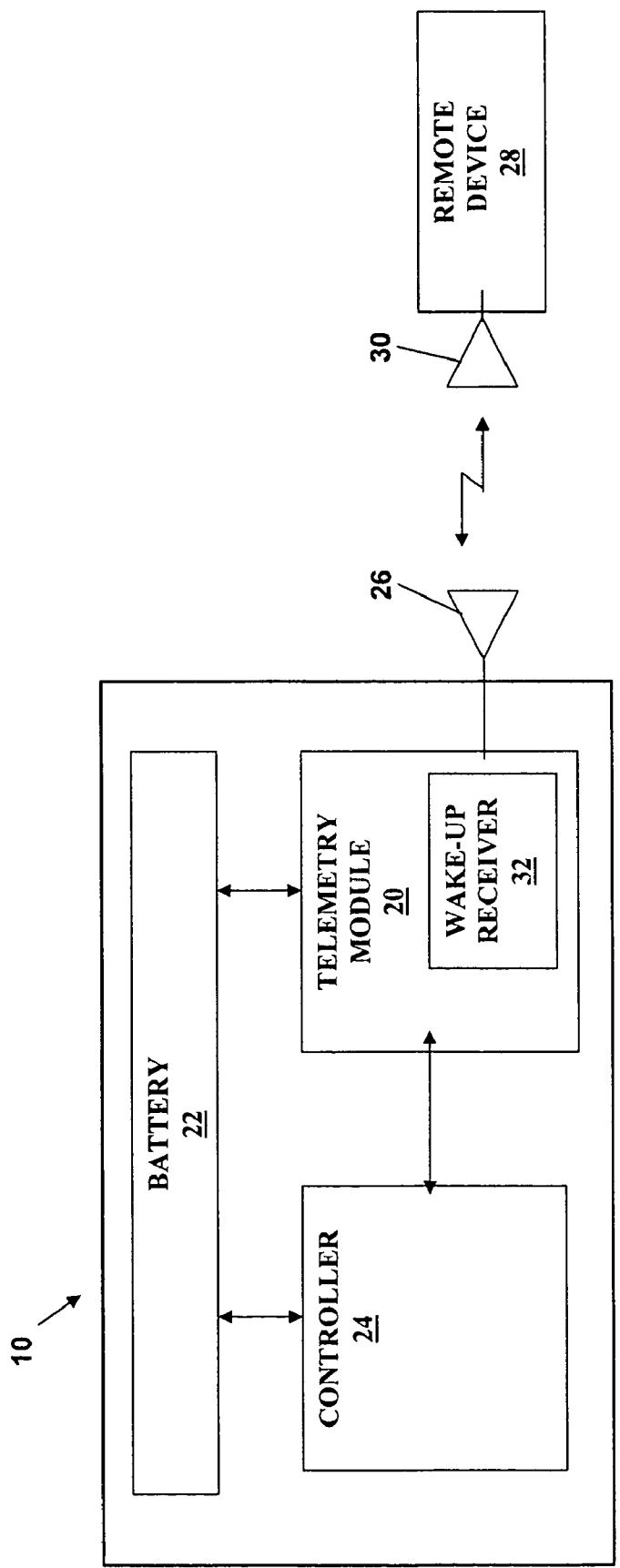
FIG. 2 is a block diagram illustrating the various components of one embodiment of an implantable medical device configured to operate in accordance with the present disclosure.

FIG. 2 is a block diagram illustrating the constituent components of IMD 10 in accordance with one embodiment having a microprocessor-based architecture. IMD 10 is shown as including a telemetry module 20, a battery 22, and a controller 24.

Telemetry module 20 may comprise any unit capable of facilitating wireless data transfer between IMD 10 and an remote device 28, where remote device 28 may comprise an external medical device, a programming device, a remote telemetry station, a base station for IMD 10, a physician-activated device, a patient-activated device, a display device or any other type of device capable of sending and receiving signals to and from IMD 10. Telemetry module 20 and remote device 28 are respectively coupled to antennas 26 and 30 for facilitating the wireless data transfer. Telemetry module 20 may be configured to perform any type of wireless communication. For example, telemetry module 20 may send and receive radio frequency (RF) signals, infrared (IR) frequency signals, or other electromagnetic signals. Any of a variety of modulation techniques may be used to modulate data on a respective electromagnetic carrier wave. Alternatively, telemetry module 20 may use sound waves for communicating data, or may use the patient's tissue as the transmission medium for communicating with a programmer positioned on the patients skin. In any event, telemetry module 20 facilitates wireless data transfer between IMD 10 and remote device 28. Telemetry module 20 includes wake-up receiver 32 for monitoring communication channels and detecting incoming wake-up communication signals being received from remote device 28.

Controller 24 may comprise any of a wide variety of hardware or software configurations capable of executing algorithms to control telemetry module 20, wake-up receiver 32, and other components. Example hardware implementations of controller 24 include implementations within an application specific integrated circuit (ASIC), a field programmable gate array (FPGA), a programmable logic device, specifically designed hardware components, one or more processors, or any combination thereof. If implemented in software, a computer readable medium, such as a memory in the IMD 10, may store computer readable instructions, e.g., program code, that can be executed by controller 24 to carry out one or more of the techniques described herein. For example, the memory may comprise random access memory (RAM), read-only memory (ROM), non-volatile random access memory (NVRAM), electrically erasable programmable read-only memory (EEPROM), flash memory, or the like. Telemetry module 20 may likewise comprise any of a wide variety of the above-listed hardware or software configurations capable of executing algorithms for facilitating wireless telemetry.

IMDs typically must rely entirely on an implanted power source, e.g., battery 22. It is desirous to keep the physical size of IMD 10 to a minimum, which further places limitations on the size of the implanted battery 22. The various components of IMD 10 (i.e., telemetry module 20, controller 24, wake-up receiver 32) rely on battery 22 for power. For embodiments of IMD 10 that have nonrechargeable batteries 22, IMD 10 must be surgically replaced when battery 22 is fully depleted. For embodiments of IMD 10 having rechargeable batteries 22, a surgical procedure is not required when battery 22 is depleted, however, battery 22 must be recharged more frequently since it cannot store as much energy. Thus, power conservation is particularly important in IMD 10. Further, consistently powering up wake-up receiver 32 of telemetry module 20 to perform sniff operations requires electrical power which can drain battery 22 of IMD 10 at an unacceptable rate.

In one or more embodiments, IMD 10 and a method for operating the same is provided in which telemetry module 20 is normally maintained in a power off or low power inactive "sleep" state in order to conserve power. Wake-up receiver 32 is then periodically powered up to perform sniff operations in which wake-up receiver 32 monitors communication channels in the desired communication frequencies (e.g., MICS band, MEDS band or any other frequency bands) to detect wake-up communication signals or other types of communication signals being received from remote device 28. If a communication signal from remote device 28 is detected during these sniff operations, it is determined that remote device 28 is either attempting to communicate with IMD 10 or remote device 28 is within telemetry range capable of communicating with IMD 10 (e.g., remote device 28 is transmitting beacon signals that are being received by IMD 10). IMD 10 can then power up ("wake-up") the necessary components required to transmit or receive data from remote device 28.

There are generally multiple communication channels on which remote device 28 is capable of sending wake-up signals to IMD 10 (e.g., there are ten 300 kHz communication channels in the MICS band ranging from 402-405 MHz). Remote device 28 may select and use channels based upon channel availability and in order to avoid interference with other transmissions. Thus, IMD 10 is typically unaware of which communication channel has been selected by remote device 28, and wake-up receiver 32 must sniff each communication channel to detect whether a wake-up signal appears on any of the communication channels. However, consistently powering up wake-up receiver 32 to perform such sniff operations on each possible channel requires electrical power which can drain battery 22 at an unacceptable rate. Certain circuit elements in telemetry module 20 and wake-up receiver 32, such as a LNA and synthesizer, consume a relatively fixed amount of current each time wake-up receiver 32 is powered up to perform sniff operations. Thus, if wake-up receiver 32 were required to power up to sequentially sniff each communication channel for wake-up signals, the current consumed by the circuit elements of wake-up receiver 32 would essentially be increased by a magnitude of the number of individuals sniffs that are required to be performed multiplied by the current consumption required for a single sniff. For example, it could require 10 times the amount of current to sequentially sniff all 10 channels of the MICS band than would be consumed by a single sniff of a single channel.

In one or more embodiments, a low power, multiple channel mixing architecture is provided in wake-up receiver 32 that allows multiple communication channels to be simultaneously and individually sniffed for wake-up signals making use of a main receiver architecture of telemetry module 20 in addition to a Weaver receiver architecture. This arrangement allows multiple channels to be sniffed simultaneously in a low power implementation that minimizes total current consumption and hardware requirements while still maintaining good signal selectivity.

Figure 3:
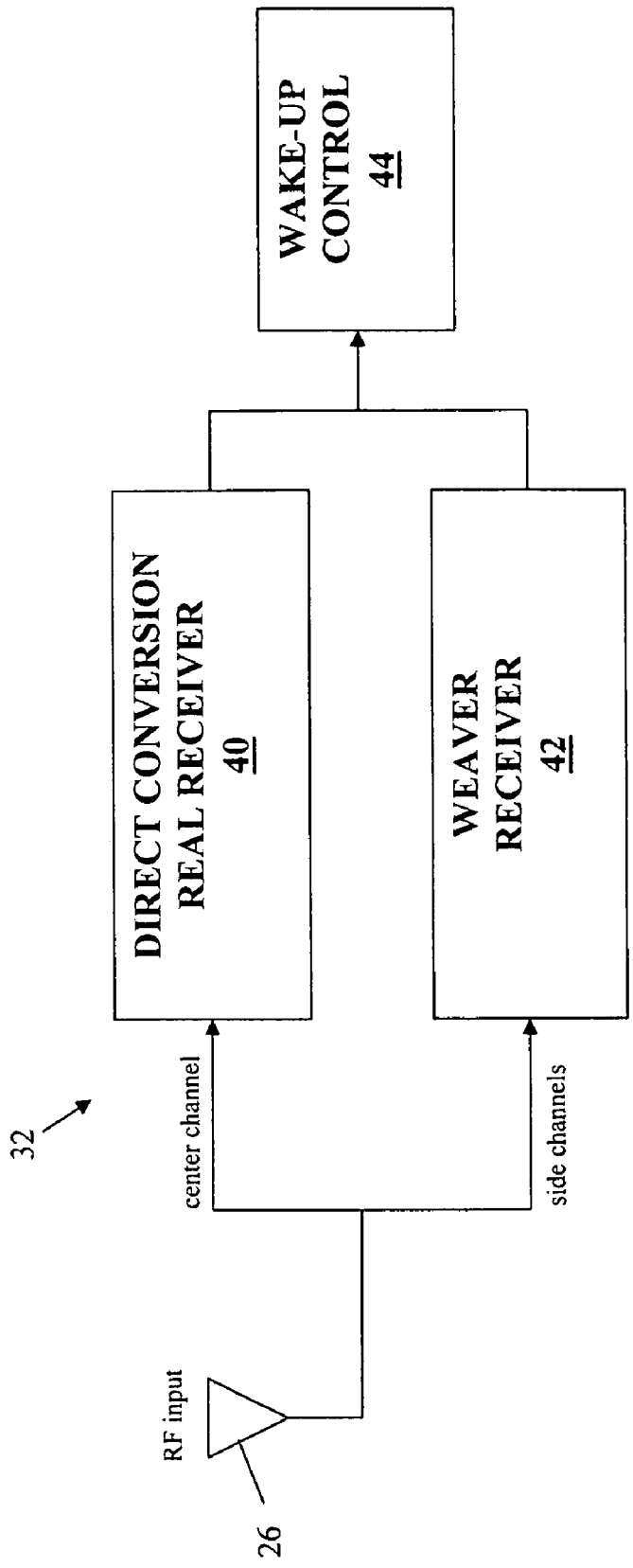
FIG. 3 is a block diagram illustrating the various components of one embodiment of the wake-up receiver of the implantable medical device configured to operate in accordance with the present disclosure.

Referring now to FIG. 3, a block schematic illustration of wake-up receiver 32 is set forth in accordance with one or more embodiments in which wake-up receiver 32 includes a direct conversion real receiver 40 and a Weaver receiver 42. In one embodiment, direct conversion real receiver 40 is a standard real direct conversion receiver circuit. When wake-up receiver 32 is activated to perform sniff operations, direct conversion real receiver 40 is configured to monitor a selected communication channel to detect whether a wake-up signal is being received from remote device 28 over the selected communication channel. While the received signal is described as including a wake-up signal, it is understood that other types of communication signals from remote device 28 can be monitored. In one embodiment, Weaver receiver 42 is a Weaver image rejecting mixer receiver circuit. Weaver receiver 42 is configured to monitor at least one communication channel adjacent to or otherwise in addition to the selected communication channel to detect whether a communication signal is being received from remote device 28 over the communication channel(s) adjacent to the selected communication channel.

In one or more embodiments, the selected communication channel to be monitored by the direct conversion real receiver 40 is considered the center channel while the adjacent communication channels monitored by the Weaver receiver 42 are considered the side channels. The RF input received over antenna 26 is delivered to both direct conversion real receiver 40 and Weaver receiver 42, which are arranged in parallel to each other so that direct conversion real receiver 40 and Weaver receiver 42 can simultaneously perform sniff operations by simultaneously scanning the incoming RF input over the selected center channel and side channels. The scanning of multiple channels simultaneously reduces current consumption in wake-up receiver 32 as opposed to performing multiple consecutive separate scans of the same channels using a single receiver. Direct conversion real receiver 40 and Weaver receiver 42 are respectively coupled to a wake-up control 44 for detecting when a wake-up signal is detected in one of the scanned communication channels and for effectuating power up ("wake-up") of the necessary components of IMD 10 required to transmit or receive data from remote device 28.

Figure 4:
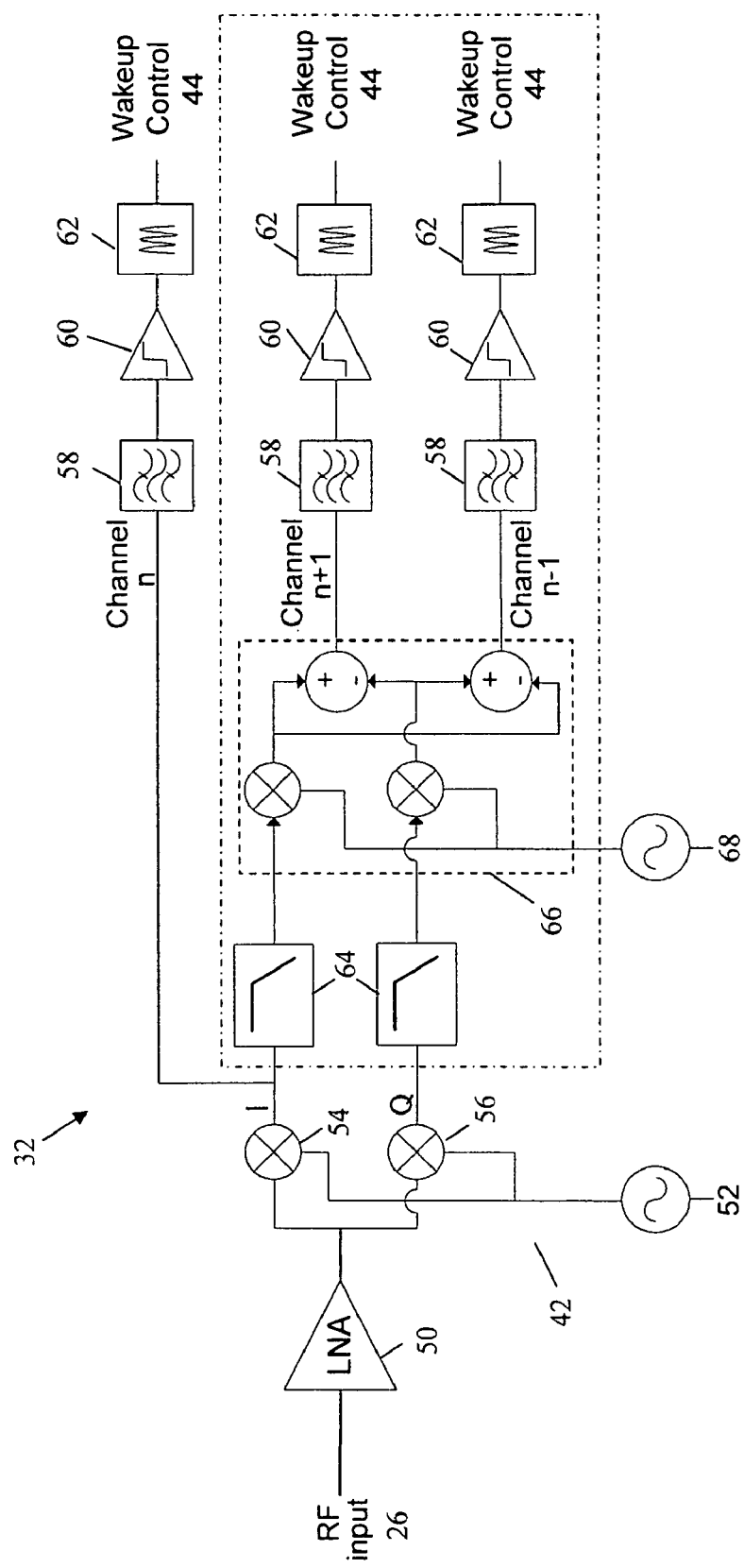
FIG. 4 is a block schematic circuit diagram illustrating the various components of one embodiment of the wake-up receiver of the implantable medical device configured to operate in accordance with the present disclosure.

Referring now to FIG. 4, a schematic circuit diagram of wake-up receiver 32 is set forth in accordance with one or more embodiments. The RF input that is received over antenna 26 is amplified with a low noise amplifier (LNA) 50 having a programmable gain (e.g., 9 dB to 35 dB or other values). Higher gain settings are preferred for IMD 10. The amplified signal is then down converted using a synthesizer 52 and mixers 54, 56 to an intermediate frequency (IF) that represents the selected center channel (n). In the typical embodiment, the center channel uses direct conversion and the IF=0 Hz. For example, a 401-406 MHz synthesizer 52 may be utilized for the MICS and MEDS bands. The signal containing the selected center channel (n) is fed through the components of direct conversion real receiver 40 that include a filter 58 used to suppress adjacent channels and limit the noise bandwidth. A limiter 60 and a wake-up signal detector 62 follow the filter 58. In one embodiment, the wake-up signal detector 62 comprises a received signal-strength indicator (RSSI) device.

The I and Q components of the down converted IF from mixers 54, 56 are utilized for the side channels monitored by Weaver receiver 42. The I and Q components are respectively fed through Weaver filters 64 and then into a Weaver mixer 66 that uses an input from a channel spacing oscillator 68 (e.g., 300 KHz in the case of MICS bands) to provide a second frequency down conversion from the first IF to the side channels. For example, the Weaver filters 64 may comprise 2 or 3 pole roofing filters that assist with spur reduction. The Weaver mixer 66 advantageously performs the second down conversion at low frequencies. Side channels (n+1) and (n−1) are generated in the illustrated example where a center channel (n) and two side channels (n+1) and (n−1) are simultaneously scanned in parallel.

Direct conversion real receiver 40 and Weaver receiver 42 only make use of real components, thereby saving power by only requiring the real portion of the communication channels to be monitored. The modulation scheme transmitted from remote device 28 should support a real single channel demodulator in order to enable more channels in parallel for a given amount of circuit area and current. In a preferred embodiment, a very low IF modulation scheme is used where the IF frequency is selected to be within a given channel. The circuit design for direct conversion real receiver 40 and Weaver receiver 42 can be variably designed to simultaneously scan any number of a plurality of communication channels in parallel based upon certain design limitations, such as the peak current consumption that can be drawn from battery 22 and also the chip size of telemetry module 20. In the existing state of technology for ULP implantable medical devices, such as IMD 10, battery 22 may have a peak current consumption value of approximately 6 mA. In one embodiment, based upon this peak current consumption value in combination with preferred minimal chip size of telemetry module 20 achievable under today's standards, total current consumption is optimally minimized by monitoring and simultaneously scanning in parallel three channels comprising a center channel and two side channels during sniff operations. However, it is understood that additional secondary mixers (i.e., Weaver mixer 66) can be added with additional oscillators 68 as permitted with peak current consumption and chip size constraints in order to increase the numbers of channels that can be simultaneously sniffed in parallel (e.g., performing 2 sniffs of 5 channels each sniff in order to sniff 10 channels).

Figure 5:
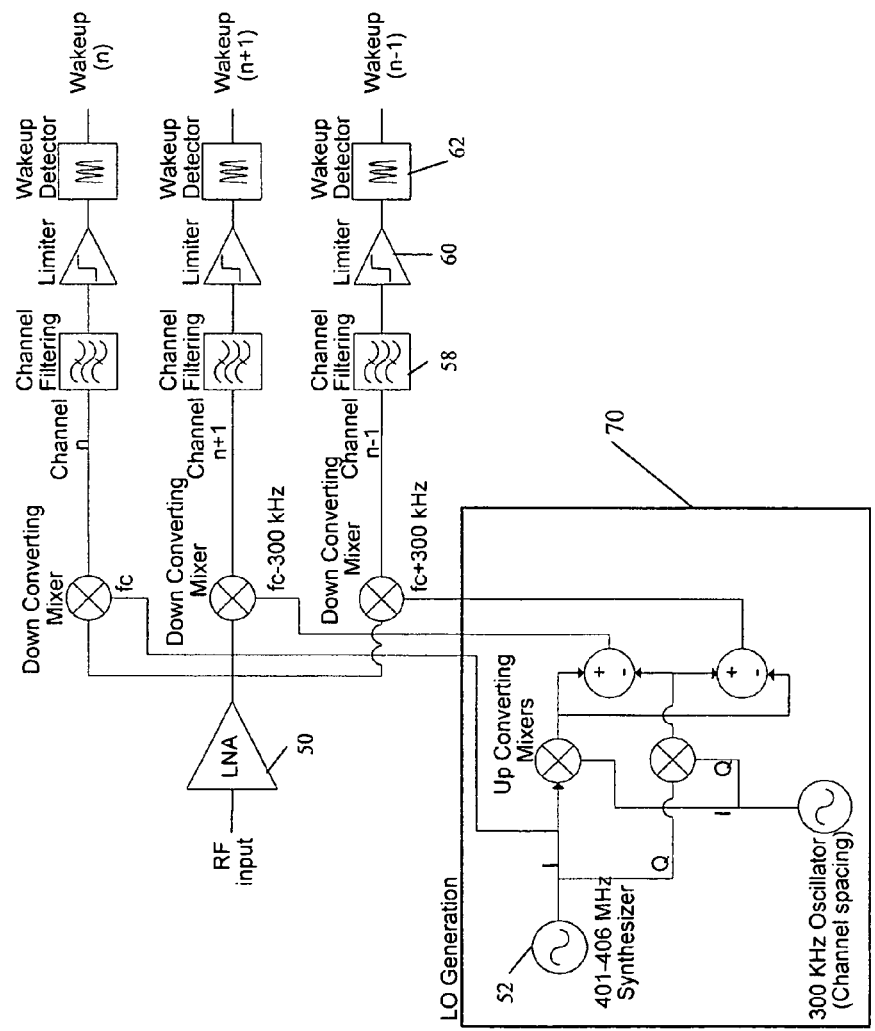
FIG. 5 is a block schematic circuit diagram illustrating the various components of another embodiment of the wake-up receiver of the implantable medical device configured to operate in accordance with the present disclosure.

Referring now to FIG. 5, a schematic circuit diagram of wake-up receiver 32 is set forth in accordance with an alternative embodiment utilizing an up-conversion local oscillator (LO) generation architecture. The RF input that is received over antenna 26 is amplified with a low noise amplifier (LNA) 50, where the amplified signal is then down converted using the output of LO generation block 70 and down converting mixers to an intermediate frequencies (IF) that represents the selected center channel (n) and side channels. The down converted center and side channels are then similarly fed through respective channel filters 58, limiters 60, wake-up signal detectors 62, and wakeup control blocks 44. The selected communication channel for the center channel $f_c$ is up-converted in LO generation block 70 using a channel spacing oscillator and up converting mixers to generate side channels (e.g., illustrated as $f_c$ −300 kHz and $f_c$ +300 kHz in the case of MICS channels in FIG. 5). This approach is advantageous in that it provides a simple reception path, re-uses normal radio circuits and consumes a minimal amount of current while simultaneously sniffing multiple channels. Up-converting mixers in LO generation block 70 should be selected and/or developed that minimize harmonic spurs that are conventionally introduced by up-converting mixers.

Figure 6:
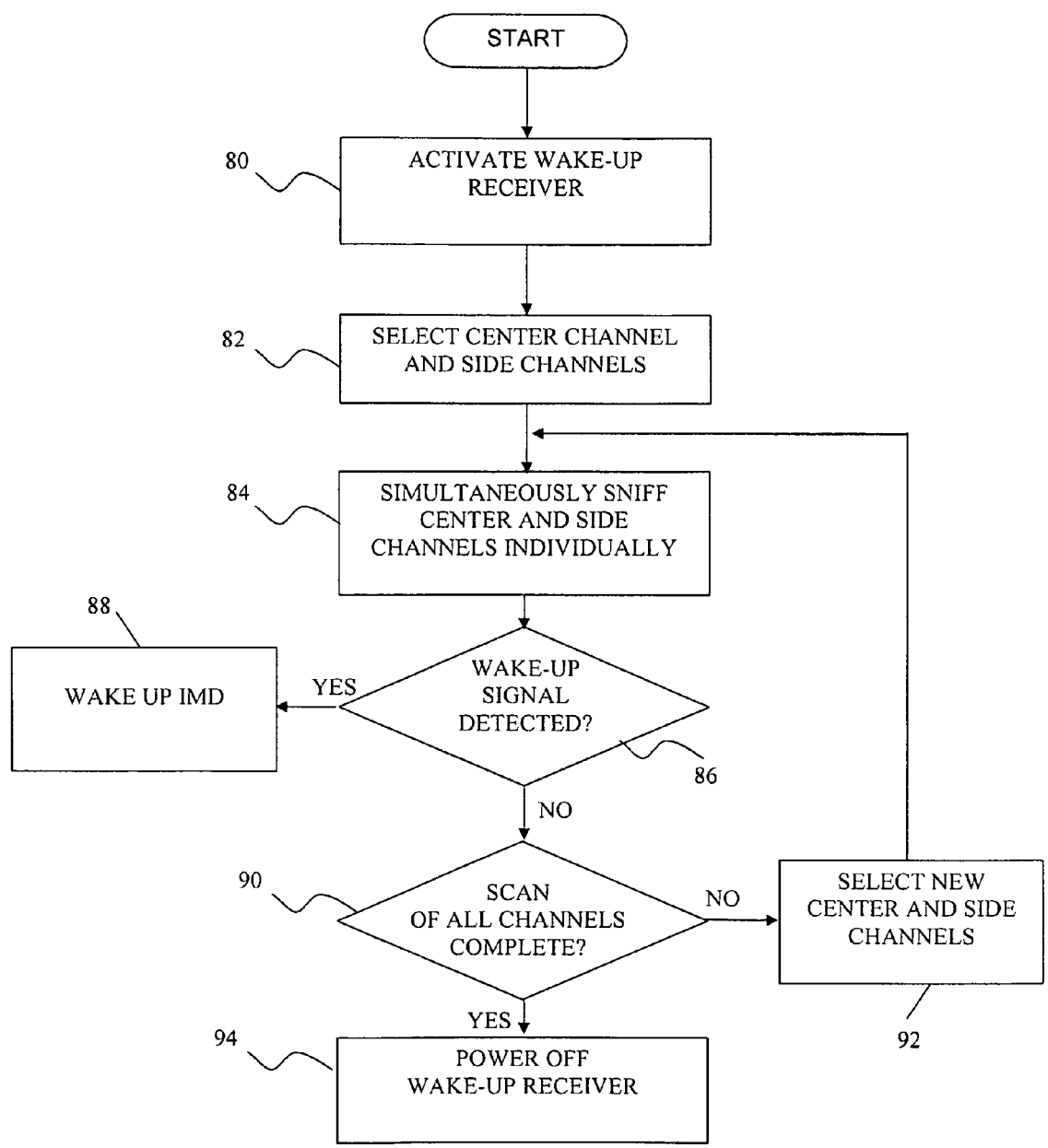
FIG. 6 is an operational flow diagram illustrating a process for operating the wake-up receiver in accordance with one embodiment of the present disclosure.

Referring to FIG. 6, an operational flow diagram for simultaneously sniffing multiple communication channels for wake-up signals while minimizing total current consumption in order to operate under ULP conditions in IMD 10 is illustrated. Wake-up receiver 32 is activated (80) for sniff operations, and the center channel (n) is selected for the selected communication channel to be scanned or monitored for detection of the presence of a wake-up signal (82). The side channel(s) adjacent (n+1, n−1) to the selected center channel (n) are further selected (82). Each of the selected center and side channels are then simultaneously scanned (84) individually. This provides preferable signal selectivity over wideband approaches that attempt to scan multiple channels all grouped together. If a wake-up signal is detected (86) in one of the scanned channels, wake-up control 44 effectuates the powering on or waking up (88) of components of IMD 10 to communicate with remote device 28. If no wake-up signal is detected (86) in one of the scanned channels, a determination is made (90) whether the preferred number of communication channels have been scanned and the scan is complete. If the overall scan is not complete, new center and side channels are selected (92) and sniffing operations are repeated for the new center and side channels. If the overall scan is complete and no wake-up signals were detected, then wake-up receiver 32 is deactivated or powered off (94) until reactivated at a later time to again perform the method of simultaneously sniffing multiple communication channels for wake-up signals as illustrated in FIG. 6.

In one or more embodiments, the scanning may be interleaved from sniff to sniff to ensure that all communication channels are ultimately scanned for wake-up signals. In one or more embodiments, the center and side channels can be selected such that there is no overlap of scanned communication channels from sniff to sniff to ensure the least number of sniffs are required to sniff all possible communication channels for the presence of wake-up signals. The center channel will generally have better quality signals than the side channels because of the harmonic spurs that can be introduced from the secondary mixers that are used in generating channel spacing for the side channels. Thus, in one or more embodiments, the communication channel that is selected as the center channel can be rotated between the various communication channels to ensure that a desired number of communication channels are at least periodically scanned as center channels instead of always being scanned as side channels.

In one or more embodiments described herein, by using a Weaver receiver architecture in combination with a direct conversion real receiver for monitoring the receipt of wake-up signals sent to IMD 10, multiple communication channels can be simultaneously scanned for wakeup signals while operating under low power conditions of less than 6 mA. Further, by using a Weaver receiver architecture in combination with a direct conversion real receiver for monitoring the receipt of wake-up signals sent to IMD 10, the main radio architecture of telemetry module 20 can be reused, thereby minimizing total current consumption and hardware requirements whilst still maintaining good signal selectivity.

Falsing Protection Algorithm

For typical RF communications, given the plethora of noise, interference sources, and other extraneous signals that exist (collectively referred to hereafter as "unwanted signals"), wake-up receiver 32 could unnecessarily consume current and thus waste the limited power resources of battery 22 if it were to implement detection procedures to discover whether these unwanted signals are actually wake-up signals. Thus, in accordance with one or more embodiments, a falsing protection algorithm is employed by wake-up receiver 32 that reduces power consumption in IMD 10 during sniff operations by inhibiting the sniffing of channels that are likely to provide a false indication of a wake-up signal. These channels are referred to as 'restricted' channels.'

Figure 7:
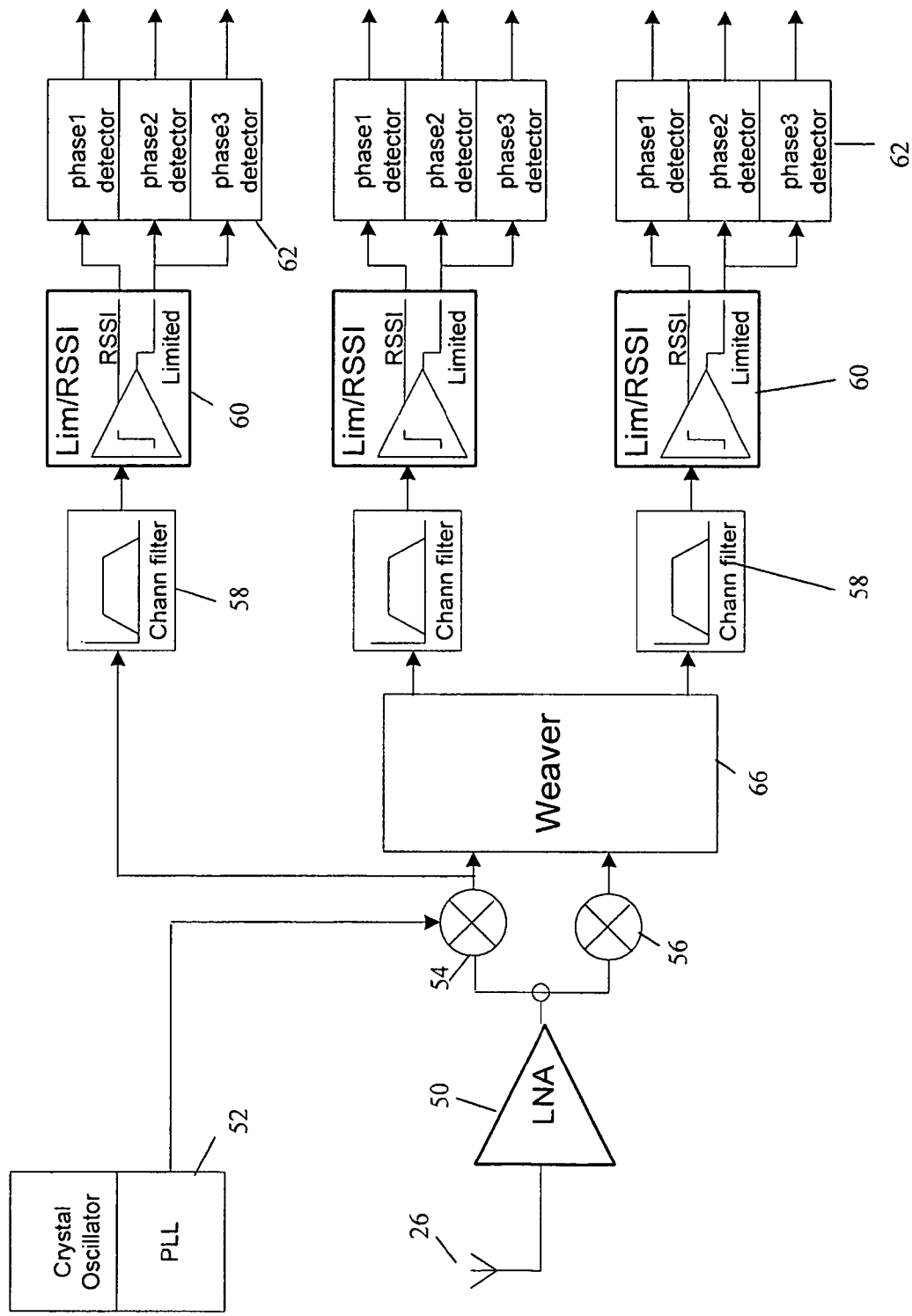
FIG. 7 is a block diagram illustrating the various components of one embodiment of the wake-up receiver of the implantable medical device including multiple phase detectors configured to operate in accordance with the present disclosure.

In one or more embodiments, a sniff is processed in a plurality of phases that are initiated simultaneously, with each stage in the progression of the phases making it increasingly difficult for noise and other unwanted signals to pass through. As illustrated in the block schematic illustration of FIG. 7, wake-up signal detector 62 may include a plurality of separate phase detectors (e.g., Phase 1 detector, Phase 2 detector, Phase 3 detector, etc.) in one embodiment. A channel becomes restricted when the sniff processing is aborted during certain phases (e.g., during Phase 2 or Phase 3) due to detection of an unwanted signal. Thus, if it is determined during certain stages of the sniff processing that the signal being processed is not a wakeup signal from remote device 28, the channel is restricted.

Figure 8A:
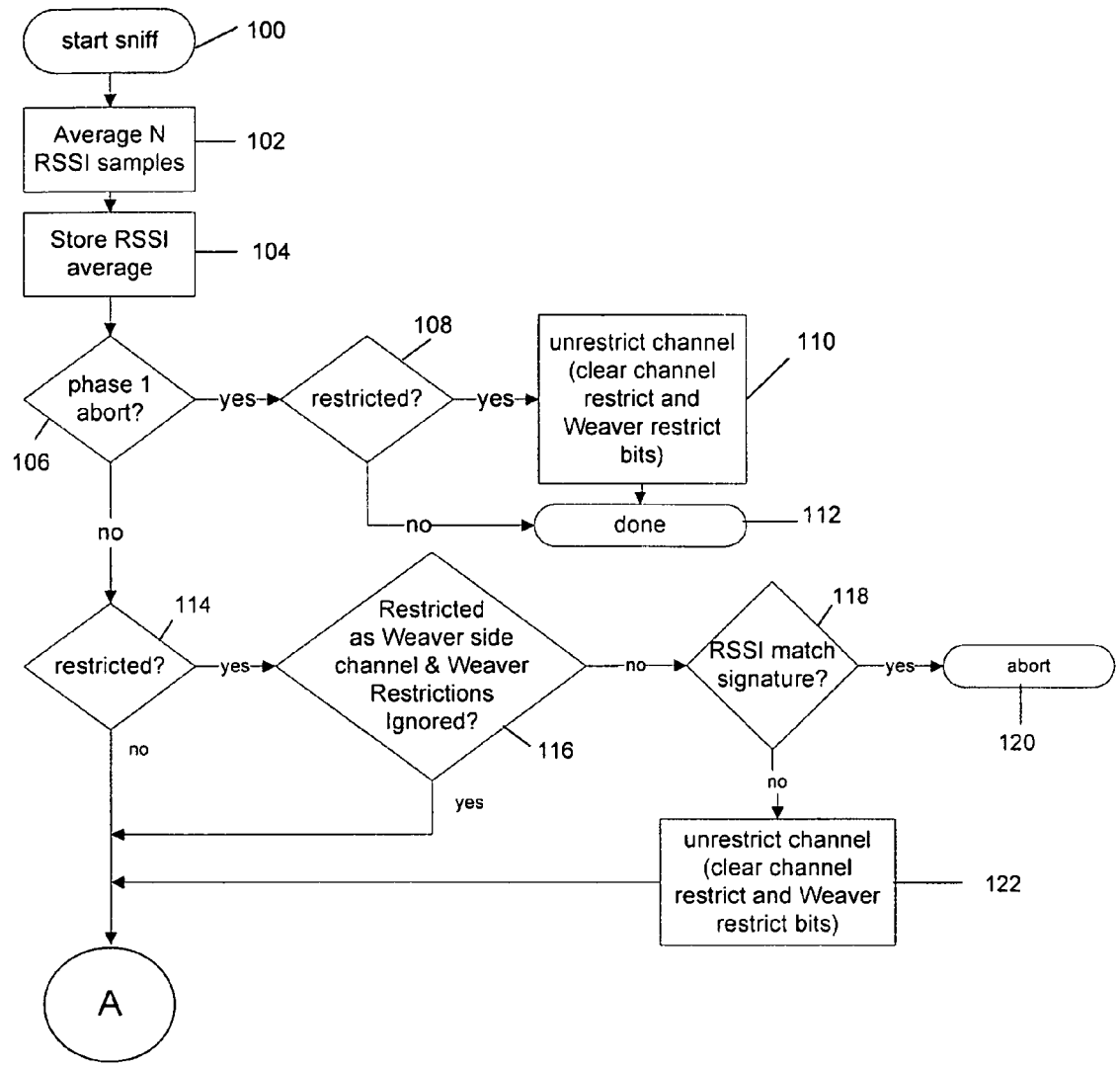
FIGS. 8A and 8B are operational flow diagrams illustrating a process for implementing a falsing protection algorithm in accordance with one embodiment of the present disclosure.
Figure 8B:
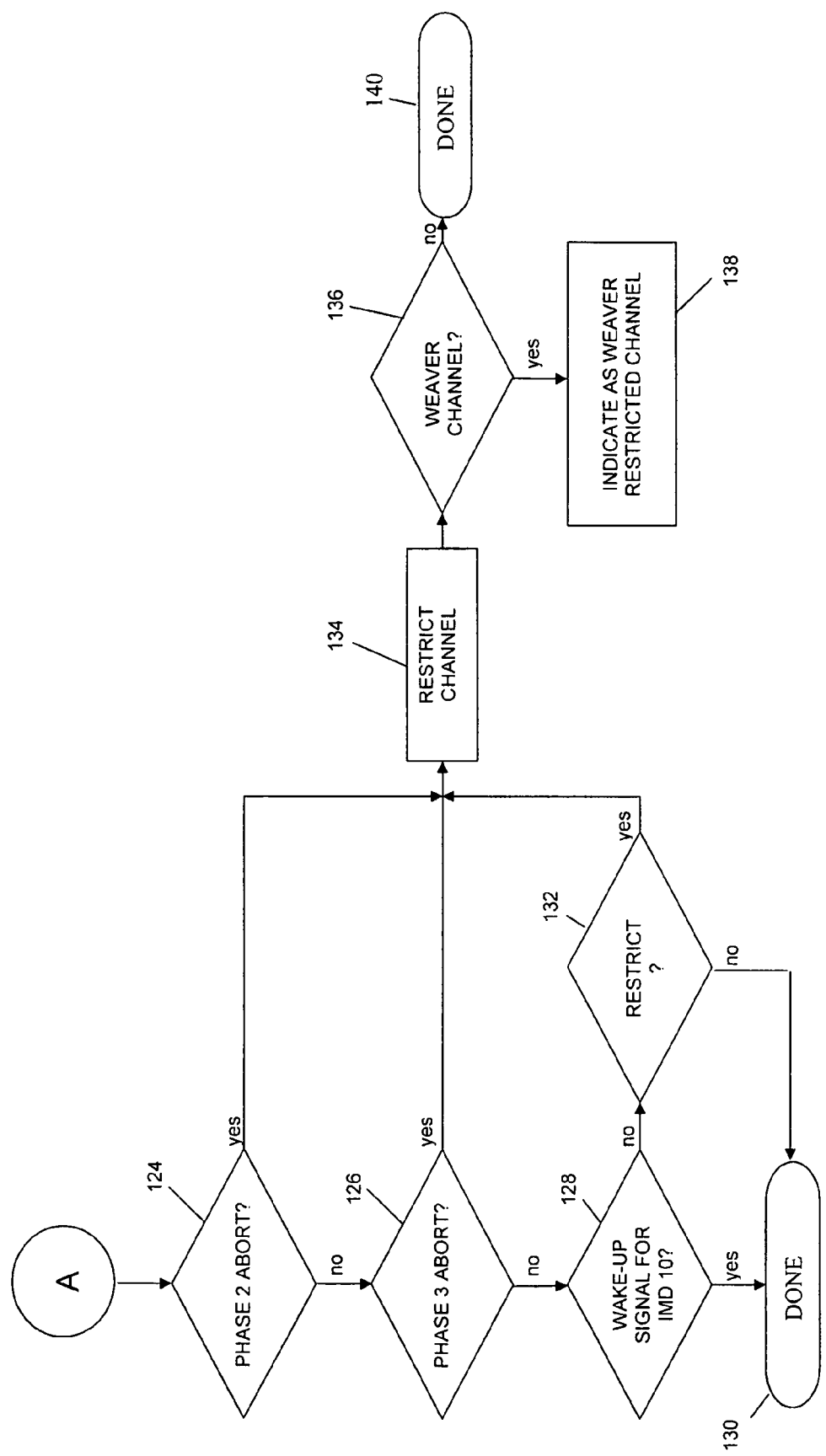
Figure 9:
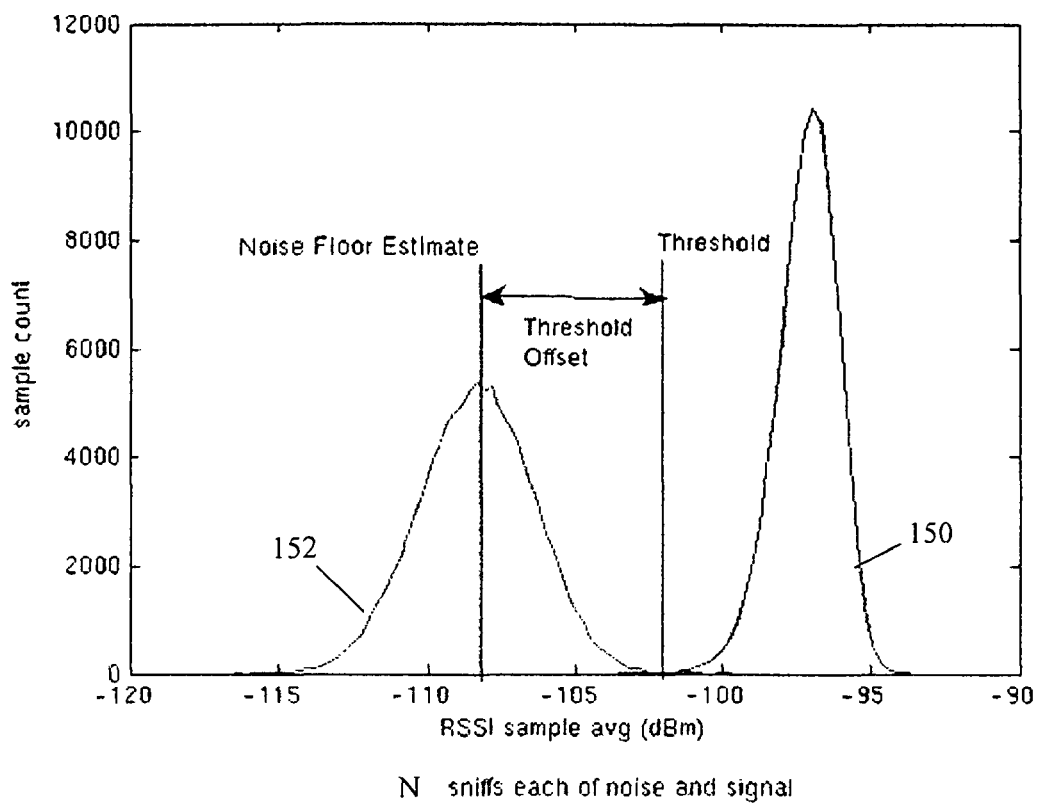
FIG. 9 is a graphical illustration of a representative RSSI sample average utilized in the falsing protection algorithm in accordance with one embodiment of the present disclosure.

An operational flow diagram is illustrated in FIGS. 8A-8B in accordance with one or more embodiments of the falsing protection algorithm. Wake-up receiver 32 of telemetry module 20 is configured to operate in a low power or power off inactive mode until wake-up receiver 32 is activated to start sniff procedures (100) to scan the center and side channels for detecting the presence of wake-up signals. In Phase 1, signal strength is measured and an average number of N (e.g., where N is programmable) Received Signal Strength Indicator (RSSI) values for the channel being scanned are measured (102) and the RSSI average is stored (104). The RSSI average of the incoming signal is compared (106) to a threshold level that is based on the estimated noise floor for that channel. As illustrated in the sample representative graphical illustration of FIG. 9, a valid wake-up signal would have an RSSI average indicated by plot 150 above the threshold level while noise and other unwanted signals would have an RSSI average indicated by plot 152 below the selected threshold. The particular threshold and threshold offset may differ based on the particular band being scanned (e.g., MICS and MEDS band may have different thresholds and threshold offsets).

If it is determined (106) that the RSSI average is below the threshold, the Phase 1 detector indicates that sniff processing should be aborted. It is then determined whether the channel being scanned is a channel that was previously restricted in a previous sniff operation (108). If the channel was not previously restricted, then sniff processing for that channel is aborted and is done (112). If the channel was previously restricted, the channel is then unrestricted (110). For example, certain information or bits associated with this channel can be stored as unrestricted or information or bits indicating that a channel is restricted can be cleared and sniff processing for that channel is done (112).

If the RSSI average is above the threshold and Phase 1 is not aborted, it is then determined (114) whether the channel being scanned is a previously restricted channel. If not previously restricted, then the falsing protection algorithm continues on with the analysis of the other phases (A) shown in FIG. 8B. If the channel is restricted, it is determined whether the channel was being scanned as a center channel or a Weaver side channel when it was previously restricted (116). If the channel is currently a center channel and it was previously restricted as a Weaver side channel and IMD 10 is configured to ignore Weaver side channel restrictions, then the falsing protection algorithm continues on with the analysis of the other phases (A). Center channels are considered to be more accurate than Weaver side channels, such that restrictions that were placed on channels when being scanned as Weaver side channels can essentially be ignored if IMD 10 is so configured so as to allow further processing of the channel to be performed. If the channel is currently a center channel and it was previously restricted as a center channel, then a RSSI signature match determination is made (118). Further, if the channel is currently a Weaver side channel and it was previously restricted as a Weaver side channel, then a RSSI signature match determination is made (118).

If IMD 10 is configured to treat all restrictions as equal regardless of whether a channel is a center channel or a Weaver side channel when it becomes restricted (i.e., IMD 10 is not configured to ignore Weaver side channel restrictions), then a RSSI signature match determination is made (118). When the channel previously became restricted, the falsing protection algorithm creates a window of values around the average RSSI level that was measured, referred to as the RSSI Signature. It is determined whether the presently scanned RSSI average is within the window of the RSSI Signature for that channel (118). If so, sniff processing is aborted (120). If the RSSI average does not match the RSSI Signature, then the channel is unrestricted (122) and the falsing protection algorithm continues on with the analysis of the other phases (A). Thus, after a channel becomes restricted, the next time that restricted channel undergoes sniff processing, the signal received must be both greater than the RSSI threshold and outside of the RSSI Signature window in order to pass Phase 1 and continue to the other phases.

In Phase 2, it is determined (124) whether the frequency deviation of the received signal on the channel being scanned is outside of an expected frequency deviation range. If the frequency deviation is outside of the expected range, then sniff processing is aborted and the channel is restricted (134). If the received signal is within the expected frequency deviation range, then Phase 3 processing of the received signal is allowed to be performed.

In Phase 3, Manchester decoding of the received signal is performed and it is determined whether the number of Manchester decoding errors exceeds a certain threshold (126). If the number of Manchester decoding errors is greater than the error threshold, then Phase 3 is aborted. If an acceptable number of Manchester decoding errors are present, then all 3 phases have passed and it is determined that the received signal is a valid wake-up signal. It is next determined (128) whether the wake-up signal received is actually intended for IMD 10 receiving the wake-up signal. If the wake-up signal is intended for IMD 10, then sniff processing is complete (130) and control is provided to wake-up control 44 to initiate wake-up procedures. If the wake-up signal was not intended for IMD 10 receiving the signal but intended for another device, then the channel can optionally be restricted. If it is determined (132) that the channel is not selected to become restricted, then sniff processing is complete (130). If it is determined (132) that the channel will become restricted, then the channel is restricted (134).

If the channel becomes restricted based on any of the determinations made in Phases 2 and 3, an RSSI Signature is created for the restricted channel that will be used in subsequent Phase 1 analyses when that channel is scanned at a later time. It is further determined whether the channel being restricted is a Weaver side channel (136) being analyzed by Weaver receiver 42. If not a Weaver side channel, then sniff processing is compete (140) for this channel. If the channel being restricted is a Weaver side channel, then an indication is associated with the restricted channel indicating that it was restricted while being scanned as a Weaver side channel (138) (e.g., by setting a Weaver restricted bit for this channel).

In one or more embodiments, all phases of the sniff processing described herein are initiated simultaneously. Some of the detection procedures performed in the various phases can be completed more rapidly than the procedures employed by the other phases. Thus, one phase may reach a determination to abort sniff processing while the other phases are still performing their respective procedures. The first phase to reach a determination to abort sniff processing will cause all of the other phases to abort sniff processing. In this manner, significant current consumption savings can be achieved alleviating wake-up receiver 32 from performing all phases of sniff processing when it becomes evident early that sniff processing should be aborted. Power consumption of wake-up receiver 32 is further reduced by avoiding sniff processing of channels that are likely to cause false alarms or false indications of wake-up signals.

The falsing protection algorithm may be implemented using a wide variety of possible hardware or software configurations. Example hardware implementations include controller 24 or other hardware implementations located in telemetry module 20 or one of its components that include implementations within an application specific integrated circuit (ASIC), a field programmable gate array (FPGA), a programmable logic device, specifically designed hardware components, one or more processors, or any combination thereof. If implemented in software, a computer readable medium, such as a memory in the IMD 10, may store computer readable instructions, e.g., program code, that can be executed by controller 24 or another hardware implementation to carry out the falsing protection algorithm described herein. For example, the memory may comprise random access memory (RAM), read-only memory (ROM), non-volatile random access memory (NVRAM), electrically erasable programmable read-only memory (EEPROM), flash memory, or the like.

While the system and method have been described in terms of what are presently considered to be specific embodiments, the disclosure need not be limited to the disclosed embodiments. It is intended to cover various modifications and similar arrangements included within the spirit and scope of the claims, the scope of which should be accorded the broadest interpretation so as to encompass all such modifications and similar structures. The present disclosure includes any and all embodiments of the following claims.

The invention claimed is:

1. A low power, multiple channel mixing architecture for a receiver in an implantable medical device comprising:
    a direct conversion real receiver circuit configured when activated to monitor a selected communication channel to detect whether a communication signal is being received from a remote device over the selected communication channel; and
    a Weaver image rejecting mixer receiver circuit configured when activated to simultaneously monitor at least one communication channel adjacent to the selected communication channel to detect whether a communication signal is being received from a remote device over the at least one communication channel adjacent to the selected communication channel.

2. The multiple channel mixing architecture of claim 1, wherein the Weaver image rejecting mixer receiver circuit is configured to monitor a plurality of communication channels adjacent to the selected communication channel.

3. The multiple channel mixing architecture of claim 2, wherein the direct conversion real receiver circuit and the Weaver image rejecting mixer receiver circuit are configured to simultaneously monitor the selected communication channel and the plurality of adjacent communication channels to detect whether a communication signal is being received from a remote device over a specific one of the monitored communication channels.

4. The multiple channel mixing architecture of claim 1, wherein the direct conversion real receiver circuit and the Weaver image rejecting mixer receiver circuit are configured to detect whether the communication signal is a wake-up signal for the implantable medical device.

5. The multiple channel mixing architecture of claim 1, wherein the selected communication channel monitored by the direct conversion real receiver circuit is a center channel, the Weaver image rejecting mixer receiver circuit further being configured to monitor adjacent side channels to the center channel.

6. The multiple channel mixing architecture of claim 1, wherein the direct conversion real receiver circuit and the Weaver image rejecting mixer receiver circuit are configured to remain in a power off state when not activated to monitor the communication channels.

7. A method comprising:
    operating an implanted medical device capable of receiving wireless communication signals;
    monitoring a selected communication channel with a direct conversion real receiver in the implanted medical device to detect whether a communication signal is being received from a remote device over the selected communication channel; and
    simultaneously monitoring at least one communication channel adjacent to the selected communication channel using a Weaver image rejecting mixer receiver in the implanted medical device to detect whether a communication signal is being received from a remote device over the at least one communication channel adjacent to the selected communication channel.

8. The method of claim 7, further comprising monitoring a plurality of communication channels adjacent to the selected communication channel using the Weaver image rejecting mixer receiver.

9. The method of claim 8, simultaneously monitoring the selected communication channel and the plurality of adjacent communication channels to detect whether a communication signal is being received from a remote device over a specific one of the monitored communication channels.

10. The method of claim 7, further comprising detecting whether the communication signal is a wake-up signal for the implantable medical device.

11. The method of claim 7, further comprising designating the selected communication channel monitored by the direct conversion real receiver as a center channel and the adjacent communication channels monitored by the Weaver image rejecting mixer receiver as side channels adjacent to the center channel.

12. The method of claim 11, further comprising:
    selecting a different center channel and respective side channels; and
    repeating the steps of simultaneously monitoring the center channel using the direct conversion real receiver and at least one adjacent side channel using the Weaver image rejecting mixer receiver to detect whether a communication signal is being received from a remote device over one of the monitored communication channels.

13. The method of claim 12, further comprising repeatedly selecting a different center channel and respective side channels and simultaneously monitoring the center channel and at least one adjacent side channel until a desired number of communication channels have been monitored.

14. The method of claim 7, further comprising operating the implantable medical device in a power off state when the direct conversion real receiver and the Weaver image rejecting mixer receiver are not activated to monitor the communication channels.

15. A method comprising:
    performing a plurality of different phases of sniff operations in an implantable medical device for detecting whether a wake-up communication signal is being received by the implantable medical device over a selected communication channel,
    wherein one of the phases of sniff operations includes a signal strength detecting phase and at least one of the other phases of sniff operations detects the presence of an unwanted signal on the selected communication channel;
    aborting all of the different phases of sniff operations on the selected communication channel if a measured signal strength in the signal strength detecting phase fails to meet a threshold value determination; and
    aborting all of the different phases of sniff operations on the selected communication channel if the measured signal strength in the signal strength detecting phase meets the threshold value determination but matches a signal strength signature associated with a previously identified unwanted signal on the selected communication channel.

16. The method of claim 15, wherein the signal strength signature comprises a range of signal strength values surrounding a measured signal strength of a previously identified unwanted signal.

17. The method of claim 15, further comprising:
aborting all of the different phases of sniff operations on the selected communication channel if the unwanted signal is detected on the selected communication channel;
restricting the selected communication channel for future sniff operations;
recording the measured signal strength of the unwanted signal; and
generating the signal strength signature of a range of signal strength values surrounding the measured signal strength for use in future signal strength detecting phases.

18. The method of claim 17, when sniff operations are aborted due to a failure of the signal strength detecting phase, the method further comprising:
determining whether the selected communication channel was identified as a restricted channel during a previous sniff operation; and
if previously identified as a restricted channel, removing the restriction from the selected communication channel so that it no longer is identified as a restricted communication channel in future sniff operations.

19. The method of claim 17, wherein sniff operations are performed by a wake-up receiver including both a direct conversion real receiver and a Weaver receiver for simultaneously performing sniff operations on a plurality of selected communication channels, when it is determined that the measured signal strength satisfies the threshold value determination, the method further comprising:
determining whether the selected communication channel was identified as a restricted channel during a previous sniff operation;
if previously identified as a restricted channel, determining whether sniff operations were being performed by the direct conversion real receiver or the Weaver receiver when identified as a restricted channel in the previous sniff operation; and
if sniff operations were performed by the Weaver receiver when the selected communication channel was previously identified as a restricted channel and if Weaver receiver restrictions are configured to be ignored, allowing the other phases of sniff operations to continue.

20. The method of claim 19, wherein if sniff operations were performed by the direct conversion real receiver when the selected communication channel was previously identified as a restricted channel and if the measured signal strength falls outside of the signal strength signature, removing any prior restrictions associated with the selected communication channel so that it no longer is identified as a restricted communication channel and allowing the other phases of sniff operations to continue.

21. The method of claim 15, wherein the at least one of the other phases of sniff operations for detecting the presence of the unwanted signal comprise at least one of a frequency deviation measuring phase and a Manchester decoding phase.

22. A telemetry module in an implantable medical device comprising:
a wake-up receiver including a plurality of signal detectors configured to perform a plurality of different phases of sniff operations in an implantable medical device for detecting whether a wake-up communication signal is being received by the implantable medical device over a selected communication channel;
at least one of the plurality of signal detectors comprising an unwanted signal detector configured to detect the presence of an unwanted signal on the selected communication channel during at least one phase of sniff operations; and
at least one of the plurality of signal detectors comprising a signal strength detector configured to perform a signal strength detecting phase during one of the phases of sniff operations,
wherein the signal strength detector is further configured to:
abort all of the different phases of sniff operations on the selected communication channel if a measured signal strength in the signal strength detecting phase fails to meet a threshold value determination; and
abort all of the different phases of sniff operations on the selected communication channel if the measured signal strength in the signal strength detecting phase meets the threshold value determination but matches a signal strength signature associated with a previously identified unwanted signal on the selected communication channel.

23. The telemetry module of claim 22, wherein the signal strength signature comprises a range of signal strength values surrounding a measured signal strength of a previously identified unwanted signal.

24. The telemetry module of claim 22, wherein the at least one unwanted signal detector is further configured to:
abort all of the different phases of sniff operations on the selected communication channel if the unwanted signal is detected on the selected communication channel;
restrict the selected communication channel for future sniff operations;
record the measured signal strength of the unwanted signal; and
generate the signal strength signature of a range of signal strength values surrounding the measured signal strength for use in future signal strength detecting phases.

25. The telemetry module of claim 24, when sniff operations are aborted due to a failure of the signal strength detecting phase, the signal strength detector is further configured to:
determine whether the selected communication channel was identified as a restricted channel during a previous sniff operation; and
if previously identified as a restricted channel, remove the restriction from the selected communication channel so that it no longer is identified as a restricted communication channel in future sniff operations.

26. The telemetry module of claim 24, wherein the wake-up receiver includes both a direct conversion real receiver and a Weaver receiver for simultaneously performing sniff operations on a plurality of selected communication channels, when it is determined that the measured signal strength satisfies the threshold value determination, the signal strength detector is further configured to:
determine whether the selected communication channel was identified as a restricted channel during a previous sniff operation;
if previously identified as a restricted channel, determine whether sniff operations were being performed by the direct conversion real receiver or the Weaver receiver when identified as a restricted channel in the previous sniff operation; and for sniff operations being performed by the direct conversion real receiver on a selected communication channel, if sniff operations were performed by the Weaver receiver when the selected communication channel was previously identified as a restricted channel and if Weaver receiver restrictions are configured to be ignored, the signal strength detector is further configured to allow the other phases of sniff operations to continue.

27. The telemetry module of claim 26, wherein if sniff operations were performed by the direct conversion real receiver when the selected communication channel was previously identified as a restricted channel and if the measured signal strength falls outside of the signal strength signature, the signal strength detector is further configured to remove any prior restrictions associated with the selected communication channel so that it no longer is identified as a restricted communication channel and to allow the other phases of sniff operations to continue.

28. The telemetry module of claim 22, wherein the unwanted signal detector comprises at least one of a frequency deviation measuring detector and a Manchester decoding detector.

* * * * *